(12) United States Patent
Korhummel

(10) Patent No.: US 11,642,041 B1
(45) Date of Patent: May 9, 2023

(54) SLOT ANTENNA SYSTEM FOR INGESTIBLE DEVICES

(71) Applicant: Verily Life Sciences LLC, Mountain View, CA (US)

(72) Inventor: Sean Korhummel, San Carlos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 496 days.

(21) Appl. No.: 16/685,936

(22) Filed: Nov. 15, 2019

Related U.S. Application Data

(60) Provisional application No. 62/771,785, filed on Nov. 27, 2018.

(51) Int. Cl.
| | |
|---|---|
| *G16H 40/67* | (2018.01) |
| *A61B 5/07* | (2006.01) |
| *A61B 5/00* | (2006.01) |
| *A61B 5/145* | (2006.01) |
| *A61B 5/03* | (2006.01) |
| *H01Q 13/10* | (2006.01) |

(52) U.S. Cl.
CPC .............. *A61B 5/07* (2013.01); *A61B 5/0031* (2013.01); *A61B 5/036* (2013.01); *A61B 5/14503* (2013.01); *A61B 5/14532* (2013.01); *A61B 5/14539* (2013.01); *A61B 5/6861* (2013.01); *G16H 40/67* (2018.01); *H01Q 13/10* (2013.01); *A61B 2560/0214* (2013.01)

(58) Field of Classification Search
CPC ......... A61B 5/07; A61B 5/0031; A61B 5/036; A61B 5/14503; A61B 5/14532; A61B 5/14539; A61B 5/68; G16H 40/67
See application file for complete search history.

(56) References Cited

U.S. PATENT DOCUMENTS

| | | | | |
|---|---|---|---|---|
| 6,632,175 | B1* | 10/2003 | Marshall | A61B 1/04 600/309 |
| 7,289,855 | B2* | 10/2007 | Nghiem | A61N 1/37229 607/30 |
| 9,270,025 | B2* | 2/2016 | Robertson | H01Q 1/08 |
| 9,489,606 | B1* | 11/2016 | Korhummel | H01Q 7/005 |
| 2020/0266528 | A1* | 8/2020 | Nikolayev | A61B 5/076 |

\* cited by examiner

*Primary Examiner* — Navin Natnithithadha
*Assistant Examiner* — Meghan R Kumar
(74) *Attorney, Agent, or Firm* — Perkins Coie LLP

(57) ABSTRACT

Introduced here is a digital pill comprised of a capsule, an ingestible sensor, and a slot antenna. The ingestible sensor can be configured to generate a signal indicative of a characteristic of the living body in which the digital pill is located. Biometric data can be stored, at least temporarily, in a memory in the form of signal values. For example, the slot antenna may transmit biometric data to a computing device across a network on a periodic basis (e.g., every 5 minutes, 15 minutes, 60 minutes, etc.). Alternatively, the slot antenna may stream biometric data to a computing device across the network in real time.

18 Claims, 11 Drawing Sheets

700

701
Insert a digital pill into a living body

702
Receive input indicative of an instruction to operate a sensor of the digital pill 703
Cause the sensor to begin generating a signal indicative of a monitored characteristic of the living body 704
Cause wireless transmission of data representative of the signal values to a receiver via a slot antenna

FIGURE 7

SLOT ANTENNA SYSTEM FOR INGESTIBLE DEVICES

CROSS-REFERENCE TO RELATED APPLICATIONS

This application claims priority to U.S. Provisional Application No. 62/771,785, titled "Slot Antenna System for Ingestible Radios" and filed on Nov. 27, 2018, which is incorporated by reference herein its entirety.

TECHNICAL FIELD

Various embodiments concern in vivo radios designed to transmit biometric data outside of the human bodies in which they are located.

BACKGROUND

Wide-scale generation of biometric data, particularly by wearable computing devices, has resulted in a greater understanding of the health of individuals. The surge in quantifiable information is likely to continue as health care evolves. A significant gap still exists, however, due to the reliance on self-reporting of such information. Accordingly, enterprises have begun developing ingestible sensors capable of automatically monitoring the human body. Biometric data generated by ingestible sensors may lend more insight into the health state on a personalized basis. For example, by examining the biometric data generated by an ingestible sensor, a medical professional (e.g., a physician or a researcher) may be able to render more informed diagnoses.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 7 depicts a flow diagram of another process for monitoring an in vivo environment using a digital pill.

Figure 1:
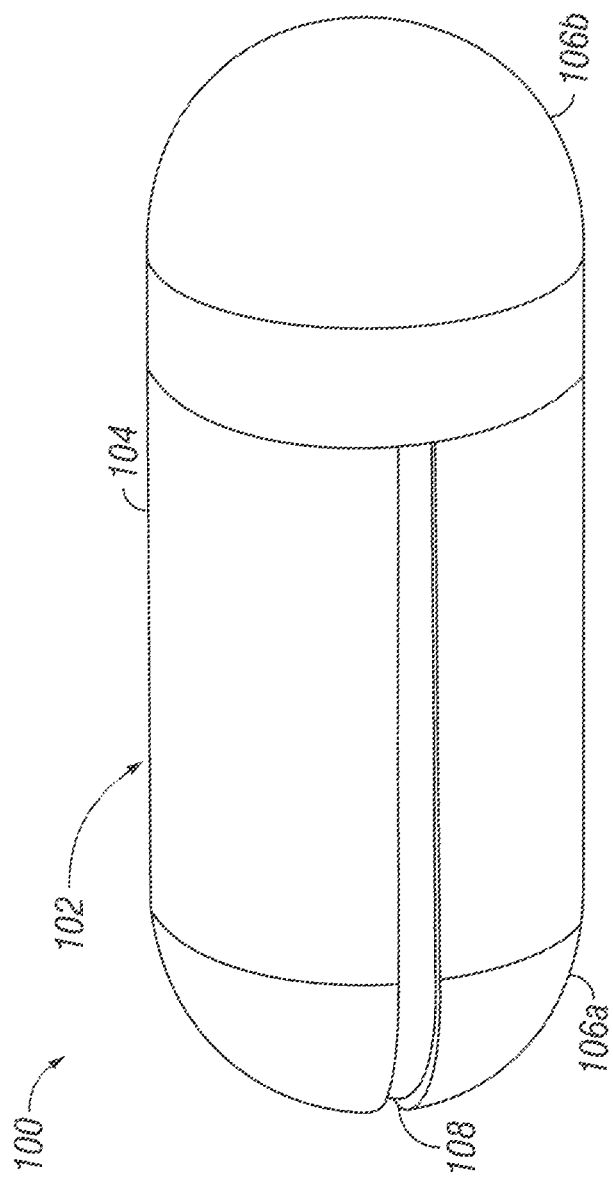
FIG. 1 depicts an example of a digital pill designed to monitor characteristic(s) of an in vivo environment in which it is located.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Contemporary research has begun exploring how to monitor in vivo environments in a more effective manner. For example, several enterprises have begun developing ingestible sensors capable of monitoring characteristics of the digestive tract. Generally, these sensors are placed in vitamin-size capsules that can be swallowed by patients. These capsules (also referred to as "digital pills") are representative of a pharmaceutical dosage form. Upon being swallowed by an individual, a digital pill may begin generating a signal indicative of a characteristic of the living body in which it is located. The digital pill can store biometric data in a memory in the form of signal values.

Transmitting the biometric data outside of the living body often proves to be problematic. For example, many antenna designs are unsuitable for use within living bodies due to the frequency, heat, required power, etc. To address these issues, digital pills are typically accompanied by a local signal receiver that is configured to forward data received from the digital pill onward to another computing device, such as a mobile phone. One example of a local signal receiver is a patch worn on the torso. Ensuring that these local signal receivers remain near the digital pills, however, can be difficult in many instances.

Introduced here, therefore, is a device (also referred to as a "digital pill" or "pill") comprised of a capsule, an ingestible sensor, and a slot antenna. The term "pill," as used herein, does not necessarily imply the inclusion of medication. Some embodiments of the digital pill may include medication, while other embodiments of the digital pill may not include medication. The ingestible sensor can be configured to generate a signal indicative of a characteristic of the living body in which the digital pill is located. Examples of such characteristics include pH, temperature, pressure, glucose concentration, medication concentration, etc. Moreover, some ingestible sensors may be configured to observe the living body itself. For example, an optical sensor could be arranged to generate video media as the digital pill traverses the living body. The term "living body," as used herein, may refer to a human body or an animal body.

Signal values representative of biometric data (or simply "data") can be forwarded to the slot antenna for transmission to a receiver located outside of the living body. More specifically, a processor may transmit the data to a transceiver responsible for modulating the data onto the slot antenna for transmission to the receiver. In some embodiments, the data is stored, at least temporarily, in a memory. For example, the slot antenna may transmit biometric data to a receiver across a network on a periodic basis (e.g., every 5 minutes, 15 minutes, 60 minutes, etc.). Alternatively, the slot antenna may stream biometric data to the receiver across the network in real time.

Generally, the receiver is part of a computing device that is associated with a subject or a medical professional, such as a general practitioner, nurse, or specialist (e.g., a gastroenterologist) who is responsible for managing/monitoring the digital pill as it travels through the living body of the subject. In some embodiments, the computing device includes a health management platform that is configured to examine the biometric data (e.g., to render diagnoses, to monitor progression of an ailment, to detect an effect of a medication, etc.). For example, the computing device may be a mobile phone associated with the subject who has ingested a digital pill, and the mobile phone may include a health management platform in the form of a mobile application. In other embodiments, the computing device is configured to forward at least a portion of the biometric data to another computing device that includes a health management platform. For example, the computing device may be a mobile phone associated with the subject who has ingested a digital pill, and the other computing device may be a network-connected server that is communicatively coupled to the mobile phone.

Embodiments may be described with reference to particular capsule shapes, ingestible sensors, computer programs, networks, etc. However, those skilled in the art will recognize that these features are equally applicable to other capsule shapes, ingestible sensors, computer programs, networks, etc. For example, although the term "mobile application" may be used to describe a computer program operable on a mobile device, the relevant feature may be embodied in another type of computer program.

Moreover, some features of the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for examining biometric data generated by an ingestible sensor, detecting variations in the biometric data indicative of a health-related event/characteristic, determining a health state based on the variations in the biometric data, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 depicts an example of a digital pill 100 designed to monitor characteristic(s) of an in vivo environment in which it is located. The digital pill 100 includes a capsule 102, which includes a cylindrical body 104 with roughly hemispherical ends 106a-b. This geometric shape may be referred to as a "spherocylinder." While the digital pill shown in FIG. 1 has roughly hemispherical ends, other hydrodynamically-shaped ends may be included in other embodiments. For example, at least one end of the capsule 102 may be a truncated cone. The cylindrical body 104 and hemispherical ends 106a-b may collectively be referred to as the "structural components" of the capsule 102. To avoid contamination of an interior cavity defined by the cylindrical body 104 and/or the hemispherical ends 106a-b, the structural components may be hermetically sealed to one another.

In some embodiments, these structural components are comprised of the same material. For example, the structural components may be comprised of stainless steel, cobalt-chromium, titanium-based alloys, or any combination thereof. In other embodiments, these structural components are comprised of different materials. For example, the cylindrical body 104 may be comprised of stainless steel, while the hemispherical ends 106a-b may be comprised of a titanium-based alloy. Moreover, these structural components may include a coating that inhibits exposure of the structural components themselves to the in vivo environment. For example, these structural components may be coated with silicone rubber. Additionally or alternatively, these structural components may be coated with an antibacterial material, such as antibiotic-loaded polymethyl methacrylate (PMMA).

As shown in FIG. 1, the cylindrical body 104 and at least one hemispherical end 106a can include an opening 108 defined therethrough that operates as a slot antenna. A slot antenna (also referred to as a "slot radiator") is an antenna that includes a conductive substrate (here, a metal surface) having a slot defined therethrough. Generally, slot antennas include an elongated slot having a length of roughly λ/2, where λ represents the resonant frequency. The resonant frequency may be based on the length of the slot, while the bandwidth of the slot antenna may be based on the width of the slot. When the conductive substrate is driven/excited at the midpoint of each longitudinal side of the slot, the slot antenna radiates electromagnetic waves in a way similar to a dipole antenna.

Due to the convenience in manufacturing, the opening 108 will often be a rectangular shape. Thus, when the capsule 102 is formed, the opening 108 may take a U-shaped form that substantially mirrors the outer surface of the capsule 102. However, the opening 108 could also have other forms. For example, in some embodiments the opening 108 has a rectangular portion with circular endpoints (e.g., similar to a barbell), while in other embodiments the opening 108 has a rectangular portion with semicircular endpoints.

The opening 108 may be designed to substantially mirror the arrangement of a conductive element that is disposed within the capsule 102. That is, the opening 108 and the conductive element may extend substantially parallel to one another at least partially along the perimeter of the capsule 102. Examples of the conductive element are discussed further below with respect to FIG. 3.

The capsule 102 may be a variety of different sizes, such as those listed in Table I.

TABLE I

Example sizes of capsules.

| | Size | | | | | | |
|---|---|---|---|---|---|---|---|
| | 000 | 00 | 0 | 1 | 2 | 3 | 4 |
| Capacity (ml) | 1.37 | 0.91 | 0.68 | 0.50 | 0.37 | 0.30 | 0.21 |
| Length (mm) | 35 | 32 | 29 | 26.5 | 24 | 21.5 | 19.5 |
| Diameter (mm) | 10 | 8.5 | 7.5 | 7 | 6.5 | 6 | 5.5 |

Figure 2:
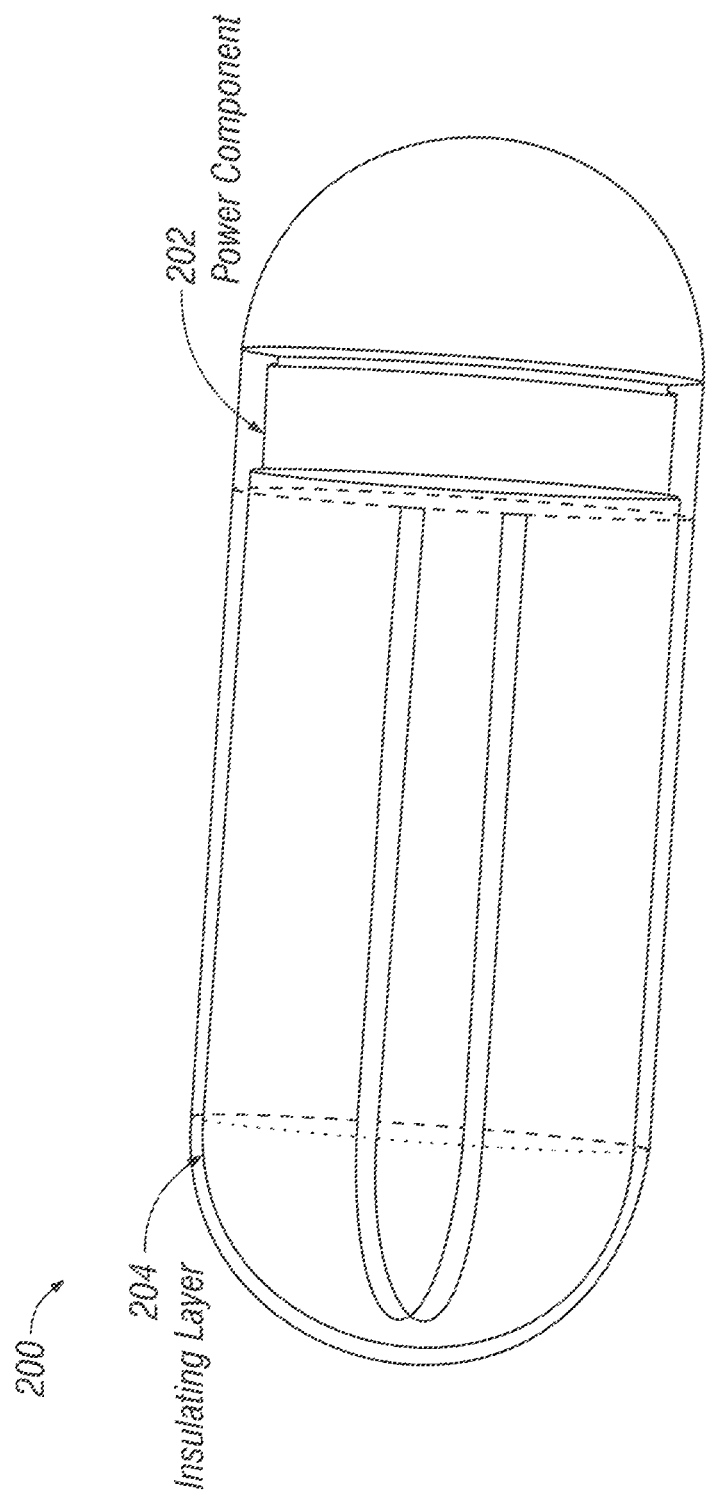
FIG. 2 depicts a cutaway view of a digital pill that includes a power component positioned near one end.

FIG. 2 depicts a cutaway view of a digital pill 200 that includes a power component positioned near one end. The power component can be configured to supply power to other components of the digital pill 200, such as any ingestible sensor(s), processor(s), communication components (e.g., transmitters, receivers, transceivers, or antennas), etc. For example, the power component may be responsible for generating the driving frequency to create electromagnetic waves via the slot antenna.

Here, the power component is a silver-oxide battery 202 in a button cell form. However, other types of power components could be used. For example, the power component could be a nickel-cadmium battery, lithium battery (e.g., with liquid cathode cells, solid cathode cells, or solid electrolyte cells), capacitor, fuel cell, piezoelectric component, or another energy-capture and/or -storage device. In some embodiments the power component includes one or more battery plates that are exposed to the fluid(s) through which the digital pill 200 travels. In such embodiments, the power component may be designed to run on a fluid (e.g., a bodily fluid such as stomach acid) that is readily accessible within the in vivo environment for which the digital pill 200 is designed. Normally, a battery operates by shuttling ions with a positive charge from one place to another through a solution called an electrolyte that has position- and negative-charged particles. In the case of exposed battery plates, however, a pair of metal electrodes can be secured to the exterior surface of the digital pill 200. One metal electrode (e.g., comprised of zinc) can emit ions into the fluid, which acts as the electrolyte by carrying a small electric current to the other metal electrode (e.g., comprised of copper).

The power component can be designed to readily fit within the capsule of the digital pill 200. For example, the silver-oxide battery 202 shown in FIG. 2 has a thickness of approximately 2.1 millimeters (mm) and a diameter of approximately 6.8 mm. Such a design allows the silver-oxide battery 202 to be secured near a hemispherical end of the capsule.

In some embodiments, the digital pill includes an insulating layer 204. The insulating later 204 may be comprised of alumina or some other material that exhibits low signal loss in the S band, such as a ceramic material. The S band is a designation by the Institute of Electrical and Electronics Engineers (IEEE) for a part of the microwave band of the electromagnetic spectrum covering frequencies from 2-4 gigahertz (GHz). Generally, the insulating layer 204 has a thickness of at least 5 mm and no more than 20 mm. However, embodiments of the insulating layer 204 may have a thickness of 5-15 mm, 6-8 mm, 8-10 mm, 10-12 mm, etc.

As shown in FIG. 1, the insulating layer 204 may be partially exposed to the in vivo environment when the digital pill 200 is deployed. For example, the insulating layer 204 may inhibit exposure of a conductive element (not shown) to the in vivo environment through an opening (e.g., opening 108 of FIG. 1) that defines a slot antenna. The insulating layer 204 may be disposed along the inner surface of the cylindrical body and one or both hemispherical ends. Here, for example, the insulating layer 204 is affixed within the cylindrical body and a single hemispherical end. However, the insulating layer 204 could also be affixed only within the cylindrical body, within the cylindrical body and both hemispherical ends, etc.

Figure 3:
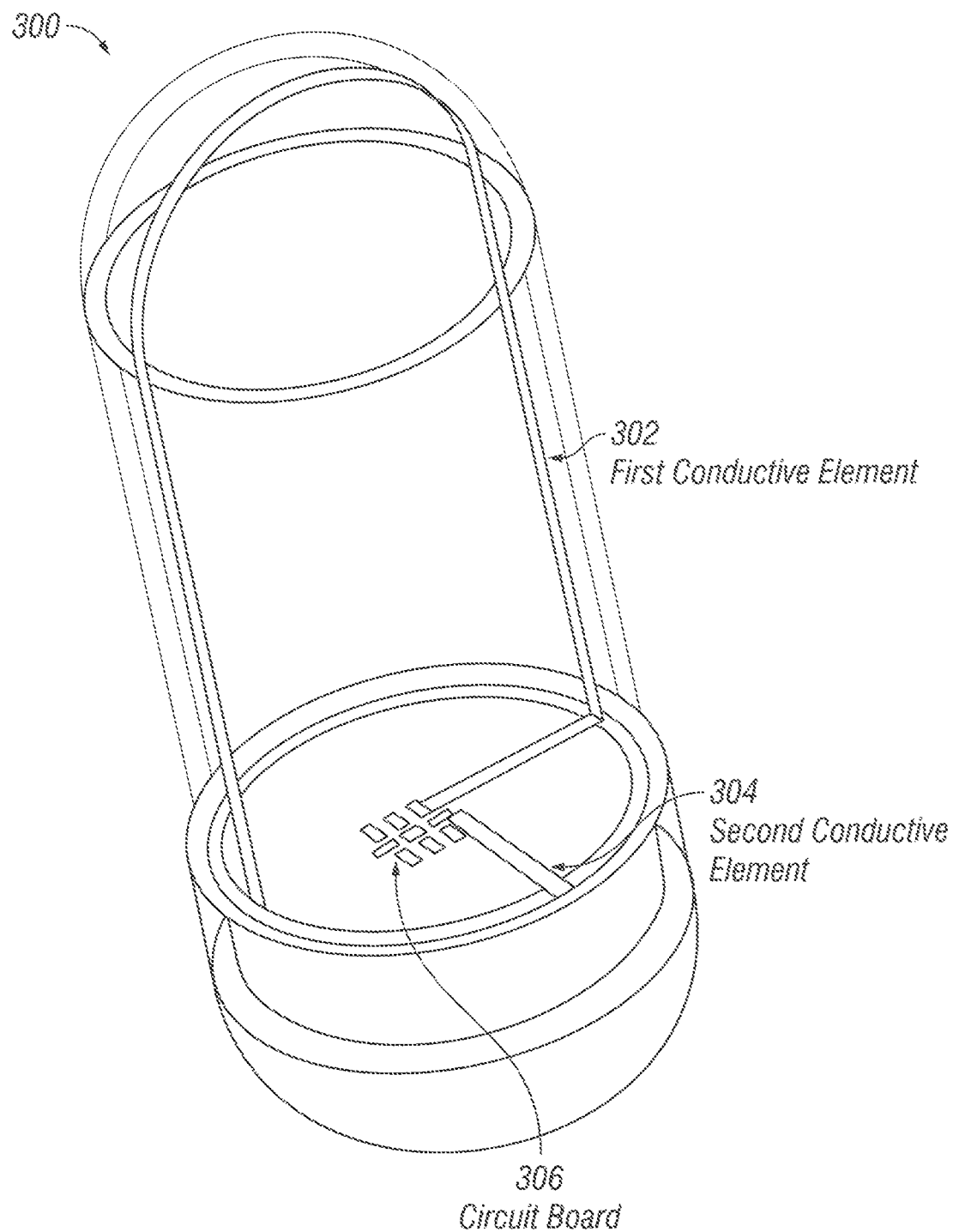
FIG. 3 depicts another cutaway view of a digital pill that includes at least one conductive element.

FIG. 3 depicts another cutaway view of a digital pill 300 that includes at least one conductive element. Here, for example, the digital pill 300 includes a first conductive element 302 and a second conductive element 304, each of which is connected to a shared circuit board 306 (also referred to as an "antenna circuit board"). The first conductive element 302 may be used as a radio frequency (RF) output to excite the slot antenna exposed along the exterior surface of the digital pill. The second conductive element 304, meanwhile, may ground the slot antenna to the outer surface of the capsule. Together, the slot antenna, first conductive element 302, and second conductive element 304 may form the complete circuit necessary for an operable radio element able to communicate, for example, within the S band.

The first and second conductive elements 302, 304 can be comprised of one or more conductive materials. Examples of such materials include copper, silver, aluminum, tungsten, nickel, gold, etc. Generally, the first and second conductive elements 302, 304 are comprised of the same material(s) for convenience in manufacturing. However, the first and second conductive elements 302, 304 could be comprised of different material(s).

Figure 4A:
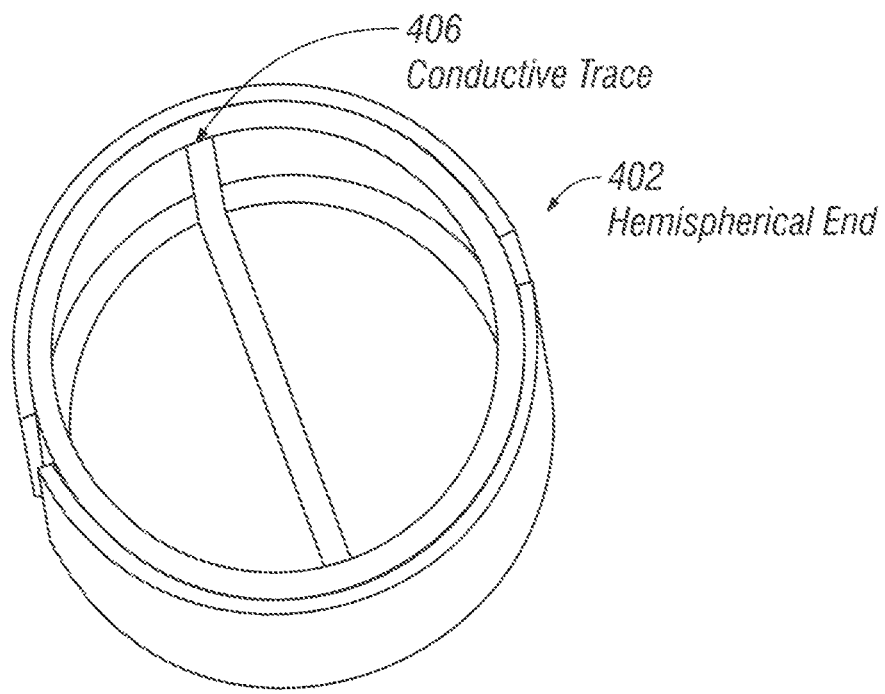
FIG. 4A illustrates a cross-sectional view of a hemispherical end of a digital pill.
Figure 4B:
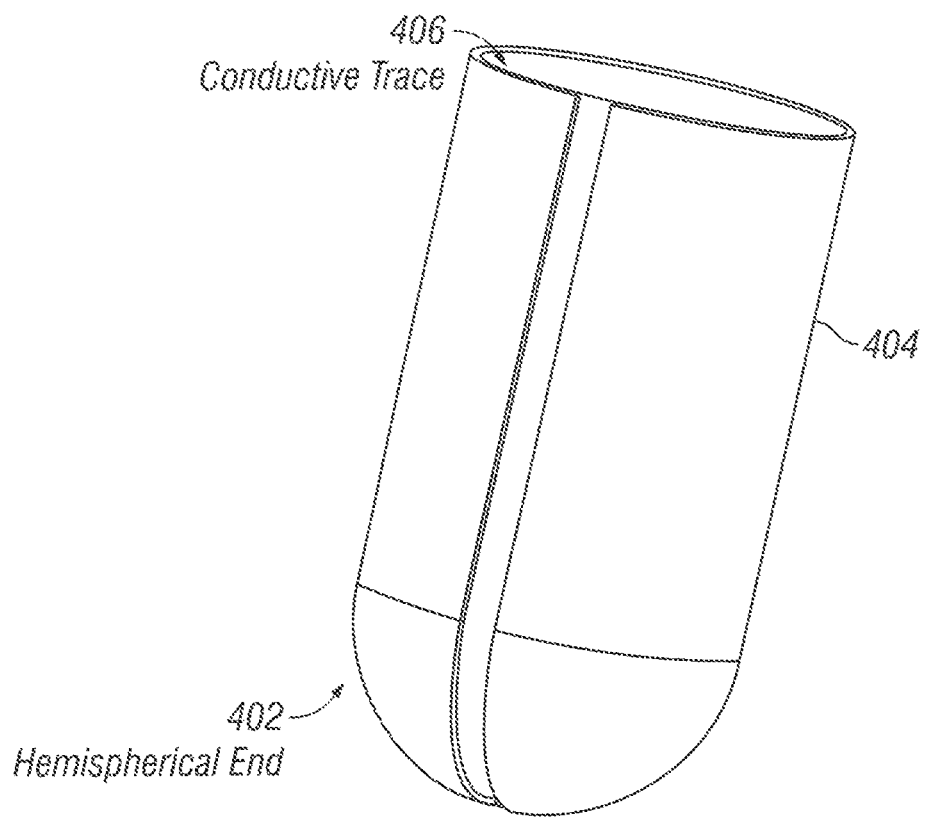
FIG. 4B includes a perspective view of the hemispherical end attached to the cylindrical body of the digital pill.

FIG. 4A illustrates a cross-sectional view of a hemispherical end 402 of a digital pill. FIG. 4B includes a perspective view of the hemispherical end 402 attached to the cylindrical body 404 of the digital pill. When connected, the hemispherical end 402 and the cylindrical body 404 may be referred to as the "bottom portion" of the digital pill. As shown in FIGS. 4A-B, the hemispherical end 402 and the cylindrical body 404 may include an insulating layer that has metal plating disposed along its exterior surface. In some embodiments, a conductive trace 406 is arranged along the interior surface of the insulating layer.

Figure 5:
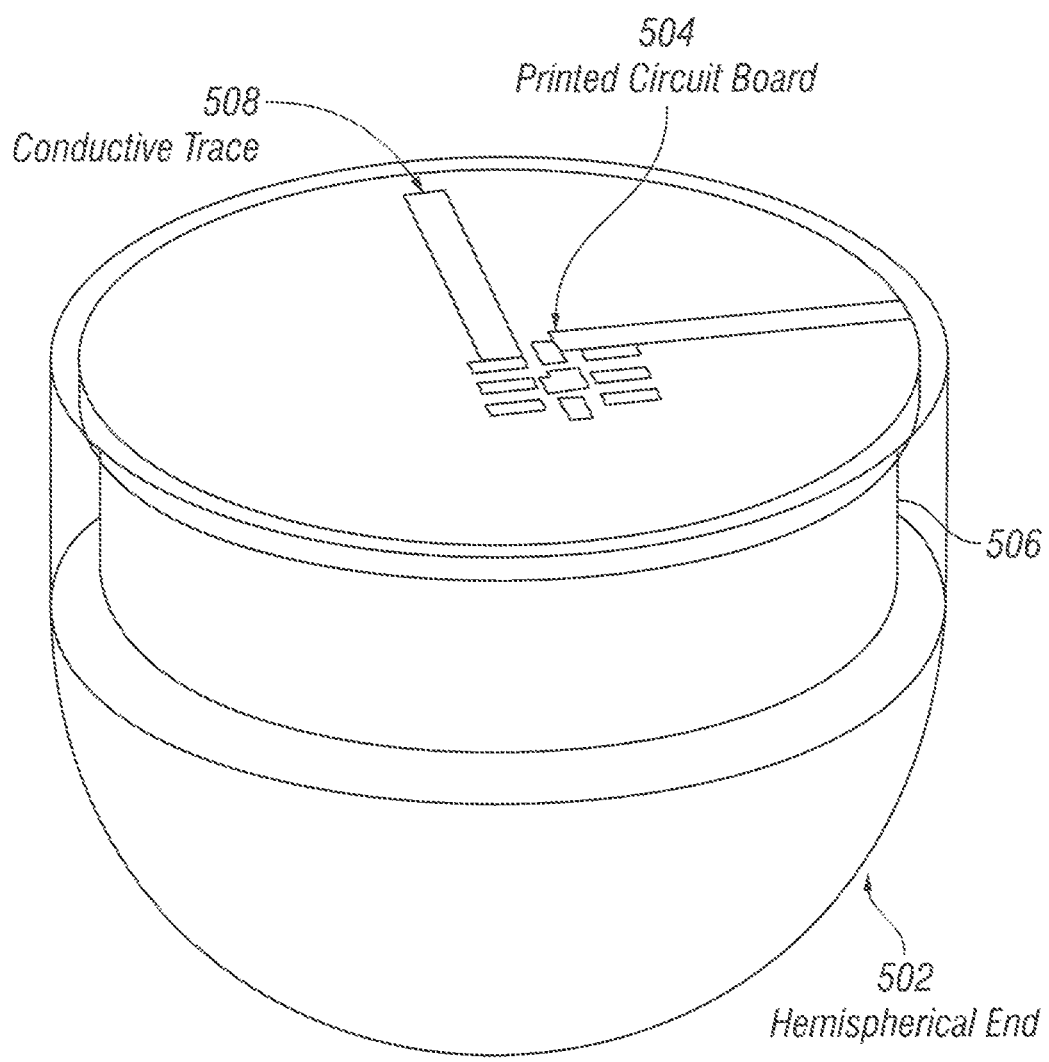
FIG. 5 includes a perspective view of a hemispherical end of a digital pill.

FIG. 5 includes a perspective view of a hemispherical end 502 of a digital pill. The hemispherical end 502 may be referred to as the "top portion" of the digital pill. The hemispherical end 502 can include a printed circuit board 504, which may include processor(s), storage module(s), etc. In some embodiments the printed circuit board 504 is grounded, while in other embodiments no ground metal is required. Vias (not shown) may extend downward from the printed circuit board 504 to the top of a power component 506. A power via may be implemented through the printed circuit board 504. For example, a first end of the power via can be connected to the power component 506, while a second end of the power via may be connected to the supply voltage (e.g., VDD) terminal of the circuitry printed on the printed circuit board 504 to provide power. Here, the power component 506 is a silver-oxide battery. In such embodiments, the battery grid can be affixed to the metal plating that forms the capsule via a soldering process, conductive epoxy, etc.

When the bottom component (as shown in FIG. 4B) and the top component (as shown in FIG. 5) are secured to one another, the hemispherical ends and the cylindrical body can define a cavity in which therapeutic substance(s) may be stored. For example, in some embodiments, the cavity includes a medication (also referred to as a "pharmaceutical drug" or "drug") designed to diagnose, cure, treat, or prevent a disease. Separation between these components (e.g., the top and bottom portions of the digital pill) may be well controlled. Thus, the components may be readily joined together (e.g., during a manufacturing process to seal in a medication). The components may be connected by aligning the conductors disposed therein (e.g., the conductive trace 406 of FIGS. 4A-B and the conductive trace 508 of FIG. 5), and then electrically joining the components.

Figure 6:
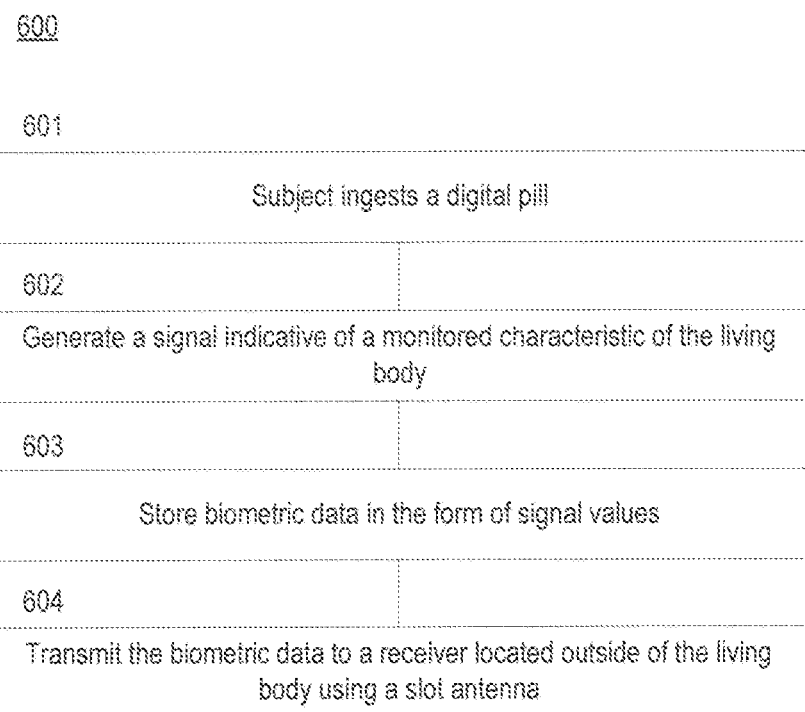
FIG. 6 depicts a flow diagram of a process for monitoring an in vivo environment using a digital pill.

FIG. 6 depicts a flow diagram of a process 600 for monitoring an in vivo environment using a digital pill. Initially, a subject can ingest the digital pill (step 601). Generally, the digital pill is designed to facilitate ingestion. For example, the digital pill may have an elongate shape with a pair of rounded ends. Moreover, the digital pill may include a coating to promote the ease/safety of ingestion. For example, the digital pill may have an antibacterial, hydrophobic, or hydrophilic coating applied thereto.

An ingestible sensor included in the digital pill can then begin monitoring a characteristic of the living body in which the digital pill is located. While monitoring the characteristic, the ingestible sensor can generate a signal indicative of the characteristic (step 602). The characteristic could be, for example, pH, temperature, pressure, glucose concentration, medication concentration, or another biometric feature. Some ingestible sensors may be configured to observe the living body itself. For example, an optical sensor could be arranged to generate video media as the digital pill traverses the living body. Examples of optical sensors include cameras equipped with complementary metal-oxide-semiconductor (CMOS) sensor assemblies capable of detecting electromagnetic radiation in the visible range, infrared sensors capable of detecting electromagnetic radiation in the infrared range, and ultrasonic sensors (also referred to as "sonar sensors") capable of detecting electromagnetic radiation in the ultrasonic range. The signal values can be stored, at least temporarily, in the form of biometric data (or simply "data") in a memory (step 603).

Thereafter, the digital pill can transmit the data to a receiver located outside of the living body using a slot antenna (step 604). The receiver may be housed within a computing device associated with the subject. For example, the data may be transmitted to a mobile phone associated with the subject, and the mobile phone may forward the data to another computing device for review by a medical professional. In some embodiments, the slot antenna transmits the data on a periodic basis (e.g., every 5 minutes, 15 minutes, 60 minutes, etc.). In other embodiments, the slot antenna transmits the data in real time. That is, the slot antenna may stream data to the computing device as the data is being generated by the ingestible sensor.

FIG. 7 depicts a flow diagram of another process 700 for monitoring an in vivo environment using a digital pill. Initially, the digital pill is inserted into a living body (step 701). For example, if the digital pill is designed to monitor the digestive system, then the digital pill may be ingested by a subject. As another example, if the digital pill is designed to monitor the cardiovascular system, then the digital pill may be inserted into a blood vessel through a small incision in the skin.

As the digital pill travels through the living body, the digital pill may receive input indicative of an instruction to operate a sensor designed to monitor a characteristic of the living body (step 702). The instruction may be received from a controller located outside the living body. The controller may be the same computing device to which signal values generated by the sensor are transmitted or some other computing device. In response to the input, the digital pill may cause the sensor to begin generating a signal representative of the monitored characteristic (step 703). Alternatively, the sensor could be configured to automatically begin generating the signal after a determination is made that the digital pill has been removed from its packaging, or after a mechanical component (e.g., a switch or a button) accessible along the exterior surface of the digital pill has been activated. For example, the sensor may begin monitoring the characteristic responsive to determining that the digital pill has been outside of its packaging for a predetermined amount of time (e.g., 3 minutes, 5 minutes, 10 minutes, etc.). As another example, the sensor may begin monitoring the characteristic responsive to determining that the digital pill has entered a particular in vivo environment. The digital pill may reach such a determination by examining data generated by another sensor. For instance, the digital pill could establish whether it is presently located in the stomach by examining data representative of pH measurements generated by a first sensor. Then, upon determining that it is located in the stomach, the digital pill could activate a second sensor configured to generate measurements for some other characteristic.

Thereafter, the digital pill can wirelessly transmit data representative of the signal values generated by the sensor to a receiver using a slot antenna (step 704). For example, a processor may transmit the data to a transceiver responsible for modulating the data onto the slot antenna for transmission to the receiver. As discussed above, the metal capsule of the digital pill may be designed to operate as the slot antenna when driven by a driving current.

Unless contrary to physical possibility, it is envisioned that the steps described above may be performed in various sequences and combinations. For example, data may be continually or periodically generated by the ingestible sensor based on the intended application. Thus, some characteristics of the human body may need to be continually monitored, while other characteristics of the human body may only need to be periodically monitored.

Other steps may also be included in some embodiments. For example, powered components (e.g., the ingestible sensor and/or the slot antenna) may be continually or periodically driven by a power component, such as a silver-oxide battery in a button cell form. However, other types of power components could be used. For example, the power component may be designed to run on a fluid (e.g., stomach acid) that is readily accessible within the in vivo environment for which the digital pill is designed. In such embodiments, the powered components may only be powered when the digital pill is within certain in vivo environments.

Figure 8:
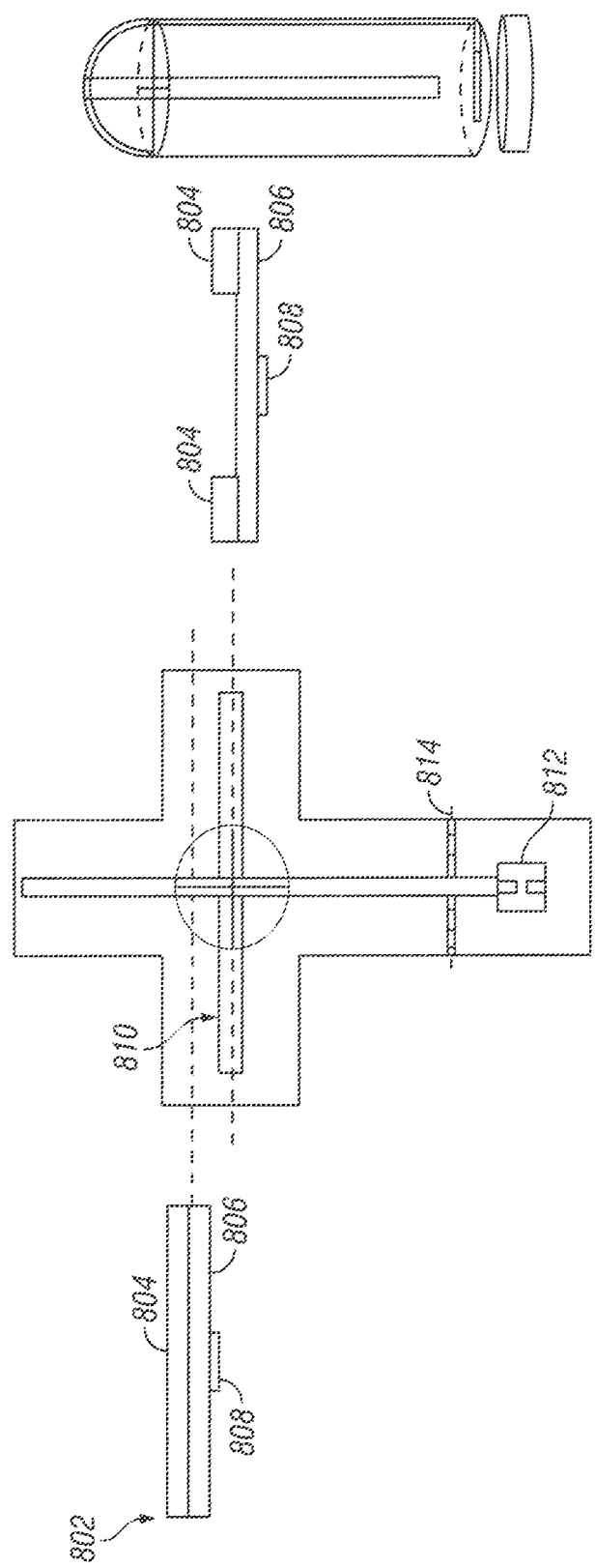
FIG. 8 illustrates a technique for manufacturing a digital pill via a roll-to-roll fabrication process.

FIG. 8 illustrates a technique for manufacturing a digital pill via a roll-to-roll fabrication process. Initially, a manufacturer acquires a flexible substrate 802 comprised of metal plating 804, an insulating layer 806 disposed beneath the metal plating 804, and a conductive metal trace 808 disposed beneath the insulating layer 806.

The flexible substrate 802 may be formed into a roughly cross-like shape that has a linear slot 810 running orthogonal to the conductive metal trace 808. When formed into a digital pill, the linear slot 810 can operate as a slot antenna. One end of the conductive metal trace 808 may be connected to an integrated circuit 812 mounted on a printed circuit board.

As shown in FIG. 8, the flexible substrate 802 may include a bend point 814 between the linear slot 810 and the printed circuit board. When the flexible substrate 802 is plunged into a gelatin cap (also referred to as a "gel cap" or "gelcap"), the arms of the cross-like shape will fold inward into the form of a capsule. Such action will cause the flexible substrate 802 to form a hemispherical end attached to a cylindrical body. The linear slot 810 may be arranged such that the geometric epicenter of the slot antenna is aligned with the geometric epicenter of the hemispherical end. Meanwhile, the conductive metal trace 808 may be arranged such that it extends across the hemispherical end and along at least one side of the cylindrical body.

The flexible substrate 802 can be bent at the bend point 814 to enclose a cavity defined by the hemispherical end and/or the cylindrical body. Here, for example, the flexible substrate 802 has been bent such that the conductive metal trace 808 forms a substantially right angle at the base of the cylindrical body. To complete the fabrication process, another hemispherical end may be secured to the base of the cylindrical body. The other hemispherical end may include, for example, a power component (e.g., a batter) that must be electrically connected to the printed circuit board.

In some embodiments, the gel cap is part of the digital pill. Thus, the molded substrate may be secured in a gel cap designed for ingestion. In other embodiments, the gel cap is removed (e.g., in favor of a silicone rubber coating). Those skilled in the art will recognize that "gel caps" are normally comprised of gelatin manufactured from collagen. However, the cap into which the flexible substrate 802 is plunged could be comprised of other materials, such as Hypromellose, Pullulan, or some other biocompatible polymer.

Figure 9:
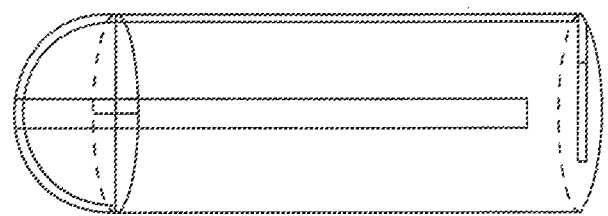
FIG. 9 illustrates another technique for manufacturing a digital pill via a roll-to-roll fabrication process.
Figure 9:
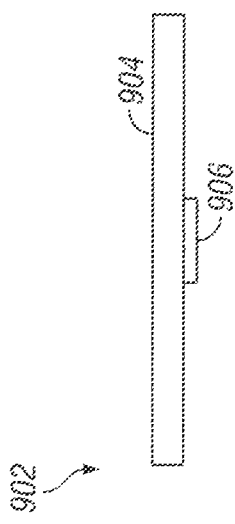
Figure 9:
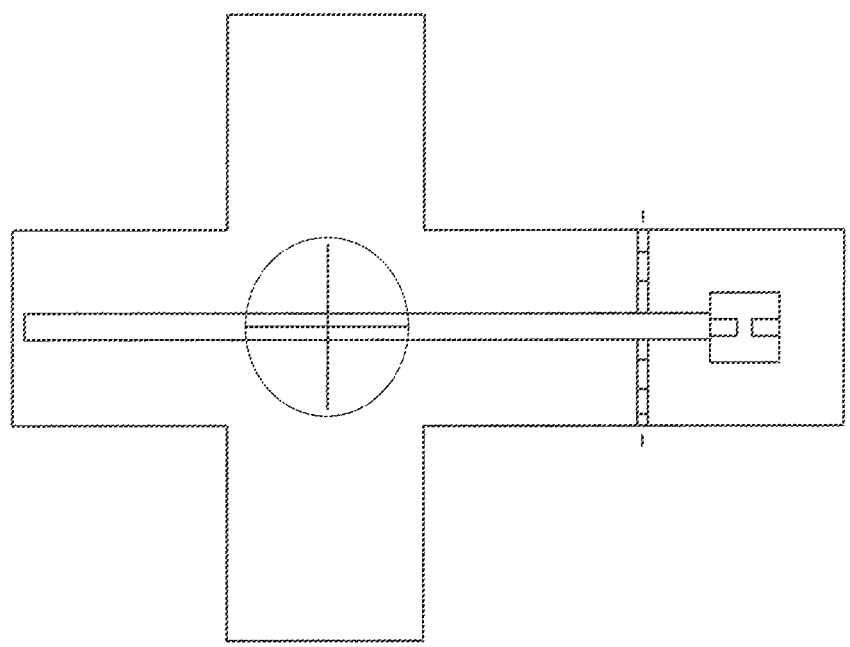

FIG. 9 illustrates another technique for manufacturing a digital pill via a roll-to-roll fabrication process. The technique shown in FIG. 9 is largely similar to the technique shown in FIG. 8. Here, however, the flexible substrate 902 is only comprised of the insulating layer 904 and the conductive metal trace 906. In such embodiments, the metal plating may be affixed to the insulating layer 904 after the flexible substrate 902 has been formed into a capsule form. For example, the metal plating may be secured to the insulating layer 904 via an adhesive film/layer, an extrusion process, etc. As another example, the gel cap into which the flexible substrate 902 is plunged may be coated with metal or some other conductive material. Such a design may reduce the strain experienced by the metal plating during the fabrication process.

Figure 10:
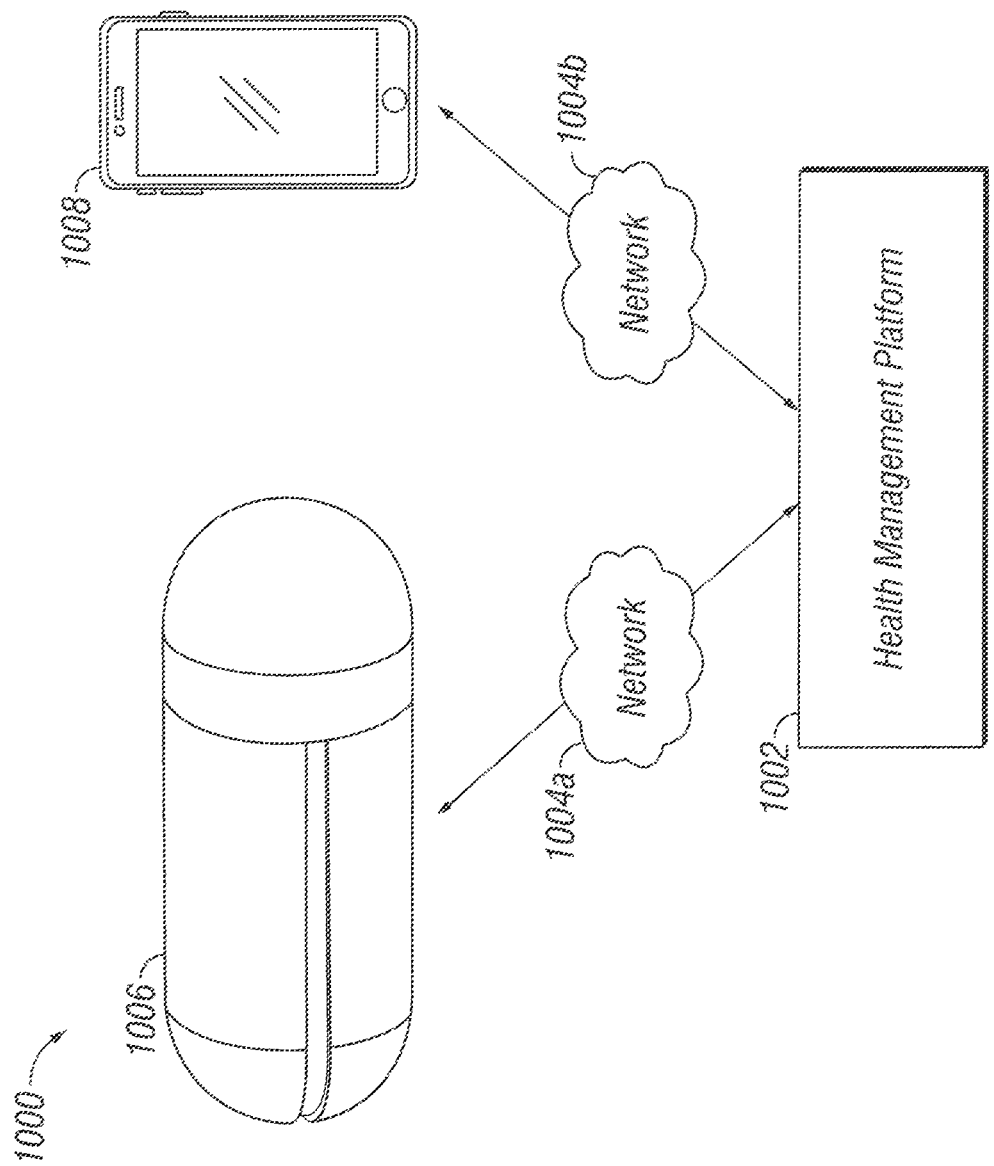
FIG. 10 depicts an example of a communication environment that includes a health management platform configured to receive biometric data from a digital pill residing within a subject.

FIG. 10 depicts an example of a communication environment 1000 that includes a health management platform 1002 configured to receive biometric data from a digital pill 1006 residing within a subject. The health management platform 1002 may also be configured to receive other data from another computing device (here, a mobile phone 1008) associated with the subject. The digital pill 1006 and the computing device may collectively be referred to as the "networked devices."

The networked devices can be connected to the health management platform 1002 via one or more networks 1004*a-b*. The network(s) 1004*a-b* can include personal area networks (PANs), local area networks (LANs), wide area networks (WANs), metropolitan area networks (MANs), cellular networks, the Internet, etc. Additionally or alternatively, the networked devices may communicate with one another over a short-range communication protocol, such as Bluetooth® or Near Field Communication (NFC). For example, the health management platform 1002 may reside on the mobile phone 1008 (e.g., in the form of a mobile application). In such embodiments, data received from the mobile phone 1008 need not traverse any networks. However, the mobile phone 1008 may be communicatively coupled to the digital pill 1006 via a Bluetooth® communication channel or a Wi-Fi communication channel.

Embodiments of the communication environment 1000 may include some or all of the networked devices. For example, some embodiments of the communication environment 1000 include a health management platform 1002 that resides on a computer server. In such embodiments, the digital pill 1006 may be configured to either transmit biometric data directly to the computer server (e.g., via a wireless access point) or transmit biometric to another computing device (e.g., the mobile phone 1008) that forwards the biometric data onward to the computer server.

Processing System

Figure 11:
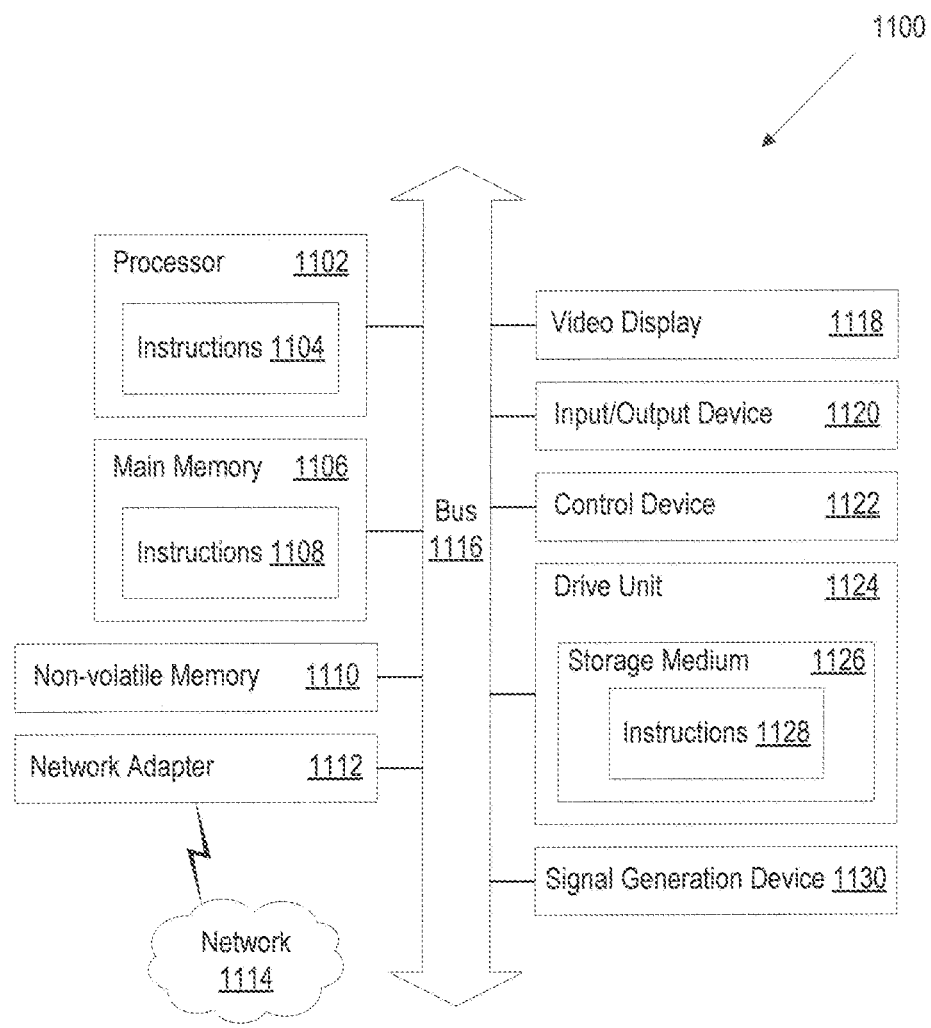
FIG. 11 is a block diagram illustrating an example of a processing system in which at least some operations described herein can be implemented.

FIG. 11 is a block diagram illustrating an example of a processing system 1100 in which at least some operations described herein can be implemented. For example, some components of the processing system 1100 may be hosted on a digital pill (e.g., digital pill 100 of FIG. 1). As another example, some components of the processing system 1100 may be hosted on a computing device that includes a health management platform.

The processing system 1100 may include one or more central processing units ("processors") 1102, main memory 1106, non-volatile memory 1110, network adapter 1112 (e.g., network interface), video display 1118, input/output devices 1120, control device 1122 (e.g., keyboard and pointing devices), drive unit 1124 including a storage medium 1126, and signal generation device 1130 that are communicatively connected to a bus 1116. The bus 1116 is illustrated as an abstraction that represents one or more physical buses and/or point-to-point connections that are connected by appropriate bridges, adapters, or controllers. The bus 1116, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1100 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1100.

While the main memory 1106, non-volatile memory 1110, and storage medium 1126 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1128. The term "machine-readable medium" and "storage medium" shall also be taken to include any medium that is capable of storing, encoding, or carrying a set of instructions for execution by the processing system 1100.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1104, 1108, 1128) set at various times in various memory and storage devices in a computing device. When read and executed by the one or more processors 1102, the instruction(s) cause the processing system 1100 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1110, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1112 enables the processing system 1100 to mediate data in a network 1114 with an entity that is external to the processing system 1100 through any communication protocol supported by the processing system 1100 and the external entity. The network adapter 1112 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1112 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A device designed for ingestion by a living body, the device comprising:

a spherocylinder capsule formed from a molded substrate that includes
an insulating layer with an inner surface that defines a cavity, and
a metal layer disposed along an outer surface of the insulating layer,
wherein the spherocylinder capsule includes a cylindrical body having hemispherical ends,
wherein the metal layer has a slot defined therethrough that extends circumferentially along one of the hemispherical ends and then longitudinally along opposing sides of the cylindrical body, so as to have a U-shaped form, and
wherein a portion of the insulating layer is exposed to an in vivo environment through the slot in the metal layer;

a sensor configured to generate signal values indicative of a biological feature; and a processor configured to:
store biometric data representative of the signal values in a memory; and
cause transmission of at least some of the biometric data to a computing device external to the living body by applying a driving current to the metal layer, wherein said application of the driving current causes the slot to radiate electromagnetic waves, thereby operating as a slot antenna.

2. The device of claim 1, further comprising:
a first conductive element disposed along the inner surface of the insulating layer.

3. The device of claim 2, wherein the processor is mounted to a circuit board secured within the cavity, and wherein the first conductive element is electrically connected to the circuit board.

4. The device of claim 2, wherein the first conductive element extends along the inner surface of the insulating layer substantially parallel to the slot defined through the metal layer.

5. The device of claim 2, further comprising:
a second conductive element configured to ground the slot antenna to an outer surface of the metal layer.

6. The device of claim 1, further comprising:
a power component configured to generate the driving current,
wherein the power component is secured within the cavity.

7. The device of claim 6, further comprising:
a power via implemented through a circuit board on which the processor is mounted,
wherein a first end of the power via is connected to the power component, and
wherein a second end of the power via is connected to a supply voltage terminal of circuitry printed on the circuit board to provide power.

8. The device of claim 6, wherein the power component is a silver-oxide button cell battery.

9. The device of claim 1, wherein the insulating layer is comprised of alumina or another ceramic material.

10. A device designed for ingestion by a living body, the device comprising:
a metal capsule having a slot defined therethrough, such that an insulating layer disposed along an inner surface of the metal capsule is partially exposed to an in vivo environment;
a sensor configured to generate signal values indicative of a biological feature;
a power component configured to generate a driving current to be applied to the metal capsule to radiate electromagnetic waves; and
a processor configured to cause transmission of data representative of the signal values to a receiver located outside the living body via the electromagnetic waves.

11. The device of claim 10, wherein the metal capsule has an elongate shape with a pair of rounded ends.

12. The device of claim 10, further comprising:
a conductive element disposed along an inner surface of the insulating layer.

13. The device of claim 12, wherein the conductive element extends along the inner surface of the insulating layer substantially parallel to the slot defined through the metal capsule.

14. The device of claim 10, wherein the metal capsule includes a cylindrical body having hemispherical ends, and wherein the slot extends circumferentially along a surface of one hemispherical end and longitudinally along opposing sides of the cylindrical body.

15. A method comprising:
receiving input indicative of an instruction to operate a sensor of a device designed for ingestion by a living body;
causing the sensor to generate signal values indicative of a monitored characteristic of the living body; and
forwarding the signal values to a transceiver for modulation onto a metal capsule of the device for transmission to a receiver,
wherein the metal capsule has an elongate body with rounded ends, and
wherein the metal capsule has a slot defined therethrough so that the metal capsule is able to act as a slot antenna when a driving current is applied thereto, the slot extending circumferentially along one of the rounded ends and then longitudinally along opposing sides of the elongate body, so as to have a U-shaped form.

16. The method of claim 15, further comprising:
storing at least some of the signal values in the form of biometric data in a memory.

17. The method of claim 15, wherein the monitored characteristic is pH, temperature, pressure, glucose concentration, or medication concentration.

18. The method of claim 15, wherein said forwarding is performed periodically so that batches of signal values are transmitted to the receiver in the form of electromagnetic waves on a periodic basis.

* * * * *